United States Patent [19]

Roggero et al.

[11] 4,450,259

[45] May 22, 1984

[54] MULTIFUNCTIONAL ANIONIC INITIATORS AND THEIR USE

[75] Inventors: Arnaldo Roggero; Mario Bruzzone, both of S. Donato Milanese; Alberto Gandini, Milan, all of Italy

[73] Assignee: Enoxy Chimica, S.p.A., Sassari, Italy

[21] Appl. No.: 450,271

[22] Filed: Dec. 16, 1982

[30] Foreign Application Priority Data

Dec. 22, 1981 [IT] Italy .................. 25751 A/81

[51] Int. Cl.³ ................................. C08F 4/46
[52] U.S. Cl. .................. 526/173; 260/665 R
[58] Field of Search ................ 526/173; 260/665 R

[56] References Cited

U.S. PATENT DOCUMENTS

| | | | |
|---|---|---|---|
| 3,193,590 | 7/1965 | Hsieh | 260/665 R |
| 4,138,536 | 2/1979 | Hsieh | 526/173 |
| 4,196,153 | 4/1980 | Tung et al. | 260/665 R |
| 4,201,709 | 5/1980 | Tung et al. | 260/665 R |

Primary Examiner—Joseph L. Schofer
Assistant Examiner—Peter F. Kulkosky
Attorney, Agent, or Firm—Hedman, Gibson, Costigan & Hoare

[57] ABSTRACT

Multifunctional anionic initiators having the general formula:

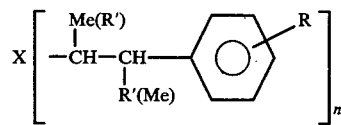

and process for synthesizing said initiators and their use in polymerizing dienic monomers and for making block polymers.

13 Claims, No Drawings

MULTIFUNCTIONAL ANIONIC INITIATORS AND THEIR USE

Many a process for producing homopolymers, statistical copolymers, grafted polymers and block polymers is known, for synthesizing well defined structures which contain particular functional groupings, said processes being based on the numerous polymerizable monomeric compounds and the different kinds of the catalytic systems.

More particularly, processes are known for polymerizing conjugates dienes which employ organic lithium-based initiators (U.S. Pat. No. 4,129,705), processes for polymerizing and copolymerizing conjugated dienes, employing an organic lithium-based initiator and a cocatalyst (BE 882.565), processes for the production of block copolymers of conjugated dienes with polar monomers, employing the products so obtained by reaction between trans-stilbene and butyl-lithium (DD-138073, DD-138071).

The anionic polymerization of diene and vinyl-aromatic polymers is known, which is intended to synthesize block polymers and telechelic polymers which are functionalized for a definite structure. To obtain polymers having satisfactory properties, it is necessary to employ quite particular catalysts which exhibit the following features, viz.
  (i) rigorously defined functionality
  (ii) solubility in hydrocarbonaceous solvents
  (iii) a fair stability, and
  (iv) a possibility of being easily synthesized.

A well defined functionality is quite a vital prerequisite for synthesizing particularly homogeneous structures. Sometimes, in fact, the catalysts having a functionality equal to or greater than 2 do not exhibit a univocally defined structure, inasmuch as there may coexist products having different functionalities and this circumstance is conducive to heterogeneous polymer products having unsatisfactory properties.

The solubility in hydrocarbonaceous solvents is an equally outstanding prerequisite because, when polymerizing conjugated diene monomers, it enables diene structures with a high 1-4 interlinking degree to be obtained, as well as polymers having the expected molecular weight.

The fair stability of the catalysts is likewise important is order that the molecular weight may be controlled and also for the economy of the process, while, lastly, their convenient accessibility has an importance from the economical standpoint.

The multifunctional catalysts, that is those having a functionality equal to or greater than 2 as known heretofore are far from possessing all the favourable features enumerated above, whereas all these prerequisites, concurrently with other advantages, are obtainable, as will be made clear hereinafter, with the catalytic systems to be described in the present application.

This invention relates to novel anionic initiators of the multifunctional class, having the general formula

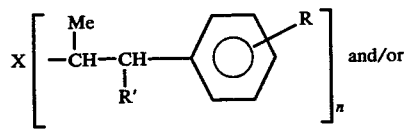 and/or

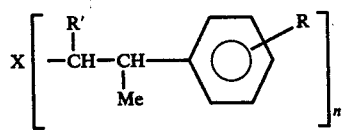

wherein:
Me is an alkali metal
n is an integer comprised between 2 and 6, the preferred values being 2 and 3,
R' is an alkyl, a hydrogen atom or an amide group and
X is a bivalent or multivalent organic radical deriving from the following structures:

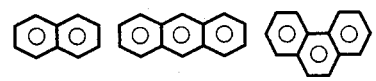

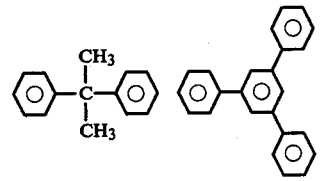

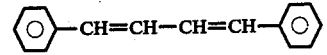

R being a hydrogen atom, an alkyl radical (preferred are those having a tertiary carbon atom directly bonded to the aromatic ring, a cycloalkyl radical an alkoxy radical or an aromatic radical and comprises from 0 to 18 carbon atoms.

The initiators are prepared starting from starting products having the general formula:

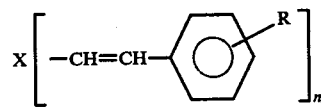

wherein X, R and n have the same meanings as defined above.

These multifunctional initiators are synthesized starting from the methyl derivatives of the structures exemplified above with X, in a simple manner and with yields which in a few cases are even quantitative, according to the procedure by A. E. Siegrist and coworkers, Helv. Chim. Acta, 52, (8), 2521 (1969).

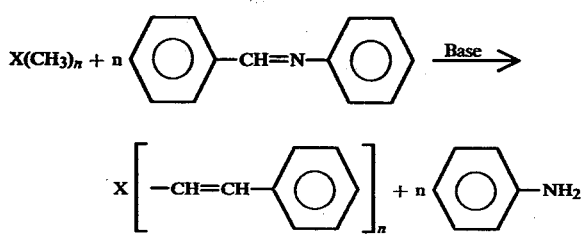

Typical examples of the methyl-containing compounds used are: 1,3-dimethylnaphthalene, 1,4-dimethylnaphthalene, 1,5-dimethylnaphthalene, 1,6-dimethylnaphthalene, 1,7-dimethylnaphthalene, 2,3-dimethylnaphthalene, 2,6-dimethylnaphthalene, 2,3,6-trimethylnaphthalene, 9,10-dimethylanthracene, 4,4'-dimethylbiphenyl, 4,4''-dimethyl p.terphenyl, 1,3,5 tri.P.tolyl benzene, dimethyl-di.p-tolylmethane, p-ditolyl ether, p.ditolylsulphide, 4,4'dimethyl trans stilbene, 1,4-di-p.tolybutadiene, 4,4'-dimethyltolane, other isomers and hologs with various substituents of the compounds enumerated above.

The di- and/or polystyryl compounds described above are then supplemented with alkyl, hydrides or amides of the alkali metals, MeR', MeH or MeNR$_2$'' (preferred are the lithium alkyls) which, by becoming bonded to the unsaturations existing in the starting compounds, form the caralysts which have the general formula:

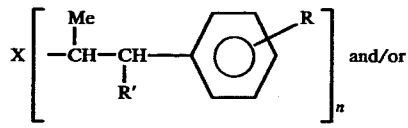

and/or

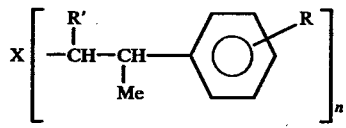

wherein X, R and n are as defined hereinbefore and Me is an alkali metal.

The lithium alkyls which are generally used are monoderivatives and vary from C2 to C12 such as ethyl lithium, nor.propyl lithium, isopropyl lithium, nor.butyl lithium, isobuty lithium, sec.butyl lithium, tert.butyl lithium, nor.amyl lithium, isoamyl lithium, sec.amyl lithium and thert.amyl lithium. Secondary and tertiary compounds are preferred. It is likewise possible to employ alkaryl lithium compounds such as benzyl lithium, 1-lithium ethylbenzene, and 1-lithium-3-methylpentyl-benzene (an adduct of lithium sec.butyl and styrene).

The ratio between these and the starting compound is a function of the type of catalyst one intended to prepare.

The catalyst-forming reaction is caused to take place in the presence of aliphatic, cycloaliphatic, aromatic, alkylaromatic solvents of admixtures thereof at a temperature comprised between 0° C. and 80° C.

As the solvents, nor.pentane, nor.hexane, nor.heptane, cyclohexane, methylcyclohexane, benzene, toluene, xylene, ethylbenzene and pseudocumene are preferred.

The reaction medium may also contain additives such as amines, preferably tertiary amines, in a ratio relative to the alkali metal, Me/N variable from 1:0.1 to 1:1.

Additives of ethereal type can also be used under such conditions as prevent secondary reactions between the metallizing compounds and the ether concerned.

The addition of two molecules of Me—R' to the compound which contains two

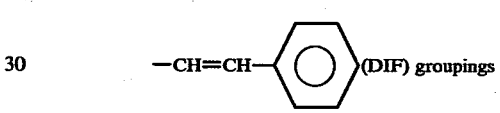

permits to prepare exactly bifunctional anionic catalysts.

The addition of three molecules of Me—R' to the compound which contains three

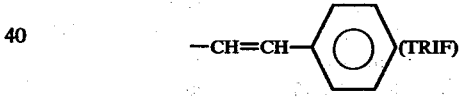

enables exactly trifunctional anionic catalysts to be obtained. These compounds can equally well be synthesized starting from the fundamental compounds DIF according to a stepwise reaction, thus:

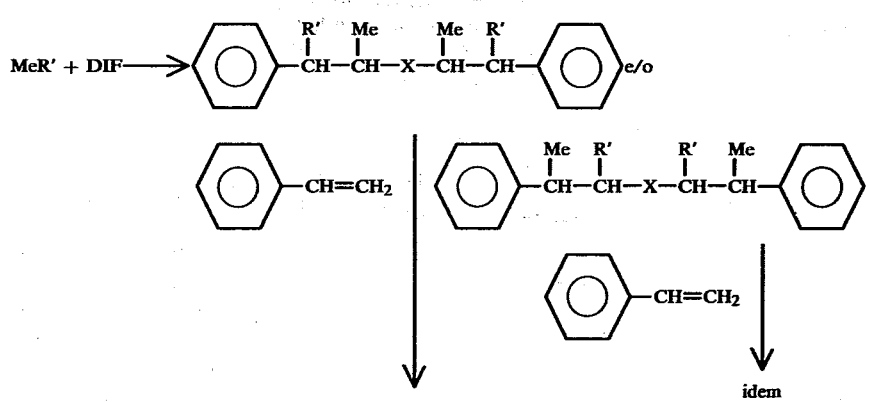

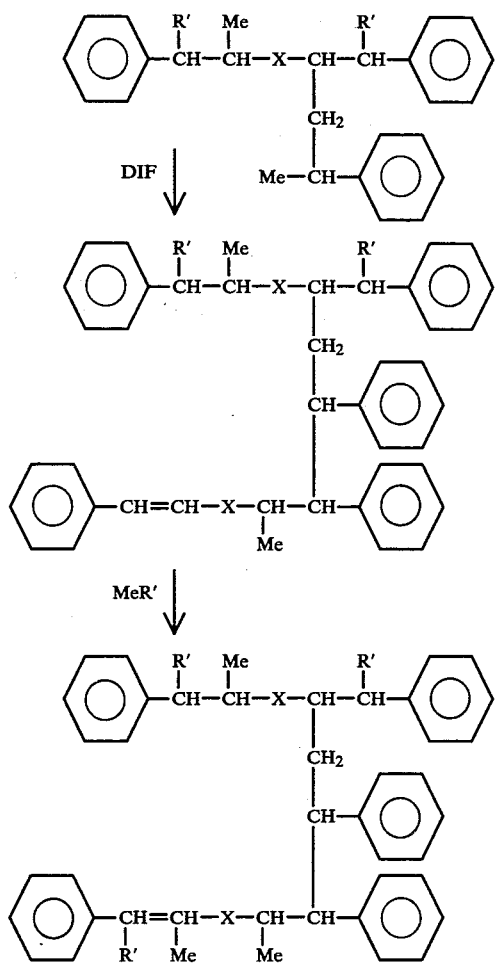

The procedure for synthesizing other polyfunctional compounds is quite similar.

The catalysts which have been described hereinbefore are soluble in the aromatic, cycloaliphatic, aliphatic solvents and admixtures thereof even without adding any polar solvents.

Sometimes, prior to storing, they are caused to interact with polymerizable compounds (P) of a diene type and/or vinylaromatic type thus originating (for bifunctional compounds) to structures of the kind:

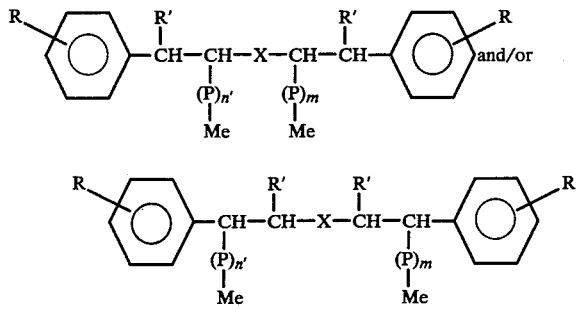

wherein n'+m is 20 and in general for other structures about 10 molecules of P per gram/atom of Me are provided.

The values of n' and m can be selected within a wide range (1 to 50).

The catalysts the subject of the present application have an excellent stability and an outstanding solubility in the hydrocarbonaceous solvents used.

Such catalysts can be used for homopolymerization, copolymerization (statistical type), especially for homogeneous class compounds, or block copolymerization for compounds belonging to non-homogeneous classes according to whether there are fed together, or sequentially, in the reaction environment, for polymerization, conjugated dienes, vinylaromatic compounds, esters, nitriles, N,N-disubstituted amides of acrylic and metacrylic compounds, vinylpiridines, vinylquinolines and their derivatives, episulphides, epoxides, lactones, lactams, siloxanes and, more generally, all those compounds which are receptive of anionic initiation.

The dienes which are used, as a rule, are: 1,3-butadiene, isoprene, 2,3-dimethyl-1,3-butadiene, 1,3-pentadiene (piperylene), 2-methyl-1,3-hexadiene and 3-butyl-1,3-octadiene. Dienes which are substituted with alkoxy groups and halogen atoms can also be used, such as: 2-methoxy-1,3-butadiene, chloroprene, fluoroprene. As vinylaromatic compounds, styrene, alphamethylstyrene, alpha-p.dimethylstyrene, 1-vinyl-naphthalene, 2-vinylnaphthalene, 4-phenylstyrene, 2-isopropenylnaphthalene, 4-phenyl-alphamethylstyrene and other compounds having several different substituents on the aromatic ring, such as alkyls, cycloalkyls, aryls, alkaryls, alkoxy, aryloxy, dialkylamino can be employed.

As episulphides, ethylene sulphide, propylene sulphide, isobutene sulphide, allyltyranyl ether can be used. As epoxides, ethylene oxide can be used. As lactones pivalolactone can be used. As lactams caprolctam can be used and as siloxanes hexamethylcyclotrisiloxane and octamethylcyclotetrasiloxane can be used.

The polymerization of such monomers takes place, as a rule, in solvents selected from among aliphatic and cycloaliphatic hydrocarbons such as pentane, heptane, hexane and cyclohexane, aromatic and alkylaromatic hydrocarbons such as benzene, toluene and xylene, aprotic polar compounds such as dimethylether, dioxan, tetrahydrofuran, furan, dimethoxyethane, diethyleneglycoldimethylether, hexamethylphophoramide, at a temperature comprised between −78° C. and the boiling point temperature of the solvent concerned.

The polymerization can also be carried out properly as a bulk polymerization.

Without involving any substantial modification of the diene structure, it is possible to use together with the solvents enumerated above, also small values (at least up to 10:1 as the ratio of compound to alkali metal) of trialkylamines, dialkyl-arylamines, diaryl-ethers and alkaryl ethers.

Inasmuch as "living" polymerizations are involved herein, the quantity of the catalyst is a function of the molecular weight of the product one intends to prepare.

The polymers which contain active —C—Me bonds can be treated with various agents which convert such active bonds into functional groups and examples of such capping agents are ethylene oxide, styrene oxide, ethylene sulphide, oxyden, $CO_2$, ethylchloroformate, allyl halides, succinic and maleic acid anhydrides, phosgene, thionyl chloride, toluene-2,4-diisocyanate and many others.

EXAMPLES

All the working details will become apparent from the perusal of the following examples. The examples, however, shall not be construed as limitations of the invention herein.

SYNTHESIZING THE POLYFUNCTIONAL ANIONIC INITIATORS

EXAMPLE 1

The reaction is carried out in a 250 ml flask equipped with a stirrer, a dropping funnel, a nitrogen inlet and an inlet for charging the reactants. There are charged 5 millimols of 2,3-bistyrylnaphthalene dissolved in 100 mls of benzene and there are added slowly dropwise at a temperature of 50° C. approximately, 10 millimols of Li-sec.butyl. After about 6 hrs, the solution, which has taken a dark purple red colour (CAT A) is split into two equal portions. A first portion is supplemented with butadiene (3 g (grams)) and allowed to stay 1 hr at a temperature of 60° C. This product (CAT A') is employed subsequently for the polymerization tests. The second portion is treated with methanol and the organic product which has thus been isolated is analyzed for M.S. and $^1$H.NMR. The Mass Spectrography data exhibit the presence of a compound having a mol wt of 448, as a result of the addition of two sec.butyl groups to a molecule of bistirylnaphthalene. The $^1$H.NMR data confirm the total disappearance of the vinyl unsaturations and the concurrent addition of the two saturated sec.butyls, the ratio of the saturated hydrogens to the aromatic being 24:16.

EXAMPLE 2

The reaction is carried out as described previously but using 1,3-bistyrylnaphthalene. Within 6 hrs there is obtained the CAT B which, upon M.S. and $^1$.NMR tests exhibits the thorough addition of the sec.butyl groups to the double bonds of the stiryl groups.

EXAMPLE 3

1,5-bistyrylnaphthalene is used (5 millimols) and the reaction is carried out in benzene (50 mls) at room temperature. In the usual reaction vessels there are added 10 millimols of Li-sec.butyl together with 1 millimol of triethylamine. After 3 hrs a deeply coloured product is obtained (CAT C) which contains 2 lithium atoms per molecule of bistirylnaphthalene.

EXAMPLE 4

The apparatus of Example 1 is charged with 10 millimols of 2,3,6-tristyrylnaphthalene, 100 mls of cyclohexane and 30 millimols of Li-sec.butyl (containing 6 millimols of dimethylaniline). The reaction is carried out at room temperature for 6 hrs (CAT D) and the M.S. and $^1$H.NMR analyses (on the product which has been neutralized with $CH_3OH$) there can be seen the addition, which has taken place, of 3 molecules of Li-sec.butyl to the starting compound.

EXAMPLE 5

10 millimols of 4,4'-bistyrylphenyl dissolved in 100 mls of benzene at 60° C. are treated with 20 millimols of Li-sec.butyl (containing 10 millimols of triethylamine). After about 8 hrs a fraction of the catalyst is supplemented with butadiene (CAT F) and another fraction is characterized by treating it with a protic medium.

The M.S. and $^1$H.NMR data evidence the addition of two sec.butyl groupings to the starting compound.

EXAMPLE 6

The procedure is the same as in the previous example, with the only difference that 4,4'-bistyrylphenyl ether is used. The results are quite the same (CAT F).

EXAMPLE 7

5 millimols of 1,3,5-tristyrylbenzene-4-yl-benzene, dissolved in 150 mls of benzene are supplemented with 10 millimols of Li-sec.butyl plus 1,5 millimol of tri-nor.-butylamine.

The reaction is carried out at 60° C. during 6 hrs. A portion of the reaction product is supplemented with butadiene (at 60° C. for 1 hr) and used in the subsequent polymerization tests (CAT G) and another portion is characterized in the usual way. The complete fading out of the unsaturated vinyl bonds is experienced with the concurrent addition of three sec.butyl groupings coming from the starting compound.

POLYMERIZATION RUNS

EXAMPLE 8

A 1 liter glass reactor which has completely been deaerated and is equipped with sealtigh stirrer, temperature and pressure gauges and an inlet for feeding the reactants, is charged with 600 mls of anhydrous benzene and 1.2 millimol of CAT A' (2.4 millimols). There are now introduced 42 g of butadiene and polymerization is allowed to take place at 60° C. during 1 hr.

One sixth of this polymeric solution is placed in a nitrogen-filled reactor and supplemented with 1 ml of tetrahydrofuran and 0.4 milliequivalent of $SiCl_4$. A gel is formed at once and, after 20 minute stirring at room temperature, glacial acetic acid is added and the gel containing mixture is allowed to stand at room temperature overnight. The polybutadiene exhibits a gel contents of 70% by wt, thus confirming the bifunctional nature of CAT A'.

The five sixth of the polymeric solution are supplemented with styrene (15 g) and allowed to polymerize at 70° C. for 2 hrs. The polymer is neutralized with methanol, coagulated and dried. There are isolated 51 g of a product which, upon $^1H.NMR$ test shows a styrene contents of 29.5% by wt and the remaining polybutadiene exhibits a microstructure which is predominantly that of 1,4.

The D.S.C. analysis of the polymer exhibits two transitions which can be attributed to the polybutadiene (−86° C.) and polystyrene block (+98° C.). The Mn molecular weight appears to be about 120,000 and the $M_w/M_n$ ratio is 1.4. For elongation at break of 900% the product shows tensile strengths of 12 MPa.

EXAMPLE 9

The procedure is the same as for Example 8, the only difference being that the B catalyst (CAT B) is used. The results which have been obtained are the same as for Example 8.

EXAMPLE 10

A glass bottle having a volume of 150 mls is charged with 25 mls of cyclohexane, 25 mls of alphamethylstyrene, 0.5 ml of styrene and 10.4 g of butadiene. At room temperature there is introduced, with a sealtight syringe 0.4 milliequivalent of CAT A, which has been interacted at room temperature with 0.4 milliequivalent of dimethylether.

After 8 hrs of reaction at room temperature, there are isolated by precipitation with methanol and drying under vacuum 15.4 g of a polymer which, upon testing $^1H.NMR$ exhibits the following composition: AlphaSTY: 32.5% by weight—The polybutadiene (67.5% by wt) has a predominant 1-4 structure.

Differential Thermal Analysis exhibits two transitions, at −82° C. and at +170° C. (not sharply defined) which can be attributed to the two blocks. The $M_n$ molecular weight of the product has proven to be 102,000 and its mechanical properties at 24° C. are: an elongation at break of 580% and a tensile strength of 18 MPa and, at 100° C., an elongation at break of 610% and a tensile strengt of 9 MPa.

EXAMPLE 11

Into a mixture of tetrahydrofuran (25 mls) and methylcyclohexane (25 mls) at the temperature of −50° C. there are poured 10 g of butadiene and 4 g of 2-isopropenylnaphthalene. Catalyst CAT E is introduced (0.4 milliequivalent) and polymerization is carried out for a few hours and there are obtained 14 g of a polymer the composition of which is 2-IPN: 28.5% on a weight basis. The polybutadiene exhibits high values of 1,2-interlinkings. This product has been hydrogenated under such conditions as to modify the diene unsaturation preferentially. The $^1H.NMR$ analysis confirms the total disappearance of the unsaturations and the DSC analysis confirms the transitions: at −60° C. to be attributed to the C2-C4 copolymer, and at +220° C. which can be attributed to the poly-2-IPN. The properties of this product, including also the stability to oxidation under heat, are outstandingly good.

EXAMPLE 12

By employing the CAT F (0.5 milliequivalent), butadiene (10 g) is polymerized as dissolved in benzene (100 mls) at the temperature of −60° C. The polymer thus obtained is siphoned into a benzene solution which has been saturated with carbon dioxide and allowed to react at the temperature of −5° C. for one hour. The mixture is made slightly acidic and a polymer is isolated which appears to contain (IR data) consistent fractions of COOH groups. The $M_n$ molecular wt is near 80,000 and the microstructure has a high contents of 1-4 (88% molar). This product is dissolved in a 1:1 mixture (volume/volume) of toluene and tetrahydrofuran (200 mls) and supplemented with 0.3 milliequivalent of tetrabutylammonium hydroxide. The reaction is allowed to proceed during 15 minutes at a temperature of 60° C. whereafter 3 g of pivalolactone are added. After 2 hours there are isolated, by acidification with HCl and precipitation with methanol, 13 g of a product which contains as much as 23% of polypivalolactone by weight.

Differential Thermal Analysis exhibits for this polymer two transitions, at −86° C. and at +207° C. which can be attributed to a high 1-4 butadiene and polypivalolactone, respectively.

EXAMPLE 13

The previous example is repeated by employing the CAT D catalyst and adopting as the solvent a mixture of 100 mls composed of benzene and tetrahydrofuran (1:1 volume:volume ratio).

The procedure is the same as described hereinabove and upon isolation of the COOH-functionalized product, hydrogenation is proceeded with and a polymer is obtained which, upon $^1H.NMR$ testing does not exhibit any more unsaturations and that, at DSC examination, shows a transition at −58° C. to be ascribed to the C2-C4 polymer.

This product is treated, like the previous one, with pivalolactone and a polymer is obtained as the end product which exhibits interesting properties with particular reference to the stability to oxidation at high temperatures.

EXAMPLE 14

Into a mixture of tetrahydrofuran (50 mls), hexamethylformamide (2 mls) there are poured at a temperature of −30° C., 30 millimols of ethylene sulphide, 64 millimol of propylene sulphide and 6 millimol of allyltyranylether. There is added 0.1 millimol of CAT C and polymerization is allowed to go ahead during 8 hours at room temperature. A terpolymer is isolated, which gives quantitative yields and is completely amorphous at X-ray examination. By curing at 145° C. for 60 minutes (charged with HAF carbon black) one obtained elongations at break of 160% and corresponding tensile strenghts of 20 MPa. These products have exhibited fair properties of resistance to the action of the solvents.

EXAMPLE 15

10 g of isoprene are polymerized with 0.5 milliequivalent of CAT G in benzene at the temperature of 60° C. for 3 hours. After this time has lapsed, there is introduced in the reaction environment 0.5 millimol of ethylene oxide and the reaction is allowed to proceed during 20 minutes. On completion of this stage, there are added small amounts of aqueous hydrogen chloride, and a polymer can be isolated which proves to contain 3 hydroxyl (OH) groups per molecule.

We claim:

1. Multifunctional anionic initiators having the general formula

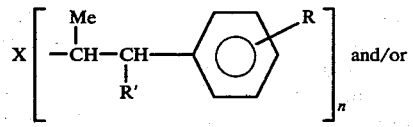 and/or

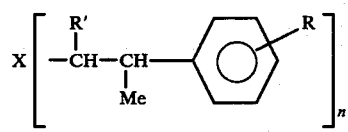

wherein
Me is an alkali metal
n is an integer comprised between 2 and 6 but is preferably 2 and 3
R' is an alkyl, a hydrogen atom or an amide group
X is a divalent or a polyvalent derivatives of the following structures:

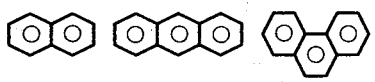

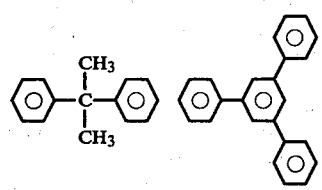

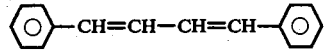

and R is hydrogen, an alkyl radical (having preferably a tertiary carbon atom directly bonded to the aromatic ring), a cycloalkyl radical, an alkoxy radical or an aromatic radical and contains from 0 to 18 carbon atoms.

2. A process for the production of anionic multifunctional initiators as defined in claim 1 consisting in reacting a compound having the general formula

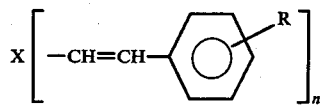

wherein X, R and n are as defined in claim 1, with alkyls or hydrides or amides of alkali metals (MeR').

3. A process according to claim 2, wherein preferably R' is an alkyl and Me is Lithium.

4. A process according to claim 2, characterized in that it is carried out in the presence of an aliphatic, cycloaliphatic, aromatic, alkylaromatic solvent or an admixture tereof.

5. A process according to claim 2, characterized in that it is carried out at a temperature comprised between 0° C. and 80° C.

6. A process according to claim 2, characterized in that amines can be present.

7. A process according to claim 6, characterized in that the amine is present in a ratio which is variable, with the alkali metal Me/n from 1:0.1 to 1:1.

8. A process for the homopolymerization or copolymerization of dienes, vinylaromatic compounds, esters or nitriles or N,N-bisubstituted amides of acrylic and metacrylic compounds, vinylpyridines or vinylquinolines and their derivatives, episulphides, epoxides, lactones, lactams, siloxanes characterized in that it employs a multifunctional anionic initiator as claimed in claim 1.

9. A process according to claim 8, characterized in that the polymerization takes place in solvents which are selected from among aliphatic, cycloaliphatic, aromatic, polar and aprotic solvents.

10. A process according to claims 8 or 9, characterized in that it is carried out at a temperature comprised between −78° C. and the boiling point temperature of the solvent concerned.

11. A process according to claim 8, characterized in that it is preferably carried out in the presence of a compound selected from among the trialkylamines, dialkylamines, diarylethers and alkarylethers.

12. A process according to claims 8 or 11, characterized in that the process is worked with a ratio of polar compound to alkali metal up to 10:1.

13. A process for the copolymerization of styrene and butadiene which comprises reacting butadiene and styrene in the presence of a compound of the formula:

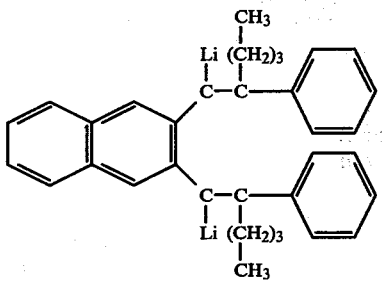

and thereafter recovering the product.

* * * * *